United States Patent
Liang et al.

(10) Patent No.: US 7,253,743 B2
(45) Date of Patent: Aug. 7, 2007

(54) TECHNIQUES FOR IDENTIFYING WHEN TO CHANGE AN AIR FILTER

(75) Inventors: Hsing-Sheng Liang, San Jose, CA (US); Saeed Seyed, Los Altos Hills, CA (US)

(73) Assignee: Cisco Technology, Inc., San Jose, CA (US)

( * ) Notice: Subject to any disclaimer, the term of this patent is extended or adjusted under 35 U.S.C. 154(b) by 161 days.

(21) Appl. No.: 11/052,383

(22) Filed: Feb. 7, 2005

(65) Prior Publication Data

US 2006/0187070 A1    Aug. 24, 2006

(51) Int. Cl.
*G08B 21/00* (2006.01)
(52) U.S. Cl. .................. 340/606; 73/195; 324/40.4; 702/33
(58) Field of Classification Search ............. 340/606, 340/607; 73/195, 196, 861.41, 863.22, 863.23; 324/71.4; 702/33, 45, 46
See application file for complete search history.

(56) References Cited

U.S. PATENT DOCUMENTS

| | | | | |
|---|---|---|---|---|
| 4,934,183 A | * | 6/1990 | Sommer et al. ........... 73/118.1 |
| 5,057,821 A | * | 10/1991 | Card ......................... 340/610 |
| 5,351,035 A | * | 9/1994 | Chrisco ..................... 340/607 |
| 5,488,811 A | * | 2/1996 | Wang et al. .................... 53/52 |
| 6,110,260 A | * | 8/2000 | Kubokawa ...................... 96/26 |
| 6,320,513 B1 | * | 11/2001 | Timmons, Jr. .............. 340/607 |
| 6,991,674 B2 | * | 1/2006 | Dietrich ........................ 96/397 |
| 2002/0078830 A1 | * | 6/2002 | Chung et al. ................. 96/424 |
| 2005/0201056 A1 | * | 9/2005 | Lin ............................. 361/695 |

OTHER PUBLICATIONS

Lin et al., Design and Analysis of an Air-Filter Sensor For a Residential Heating and Cooling System, http://www.ijme.us/issues/spring2004/Design_Analysis_AirFilter-21stEng.htm.*

* cited by examiner

*Primary Examiner*—Jeffery Hofsass
*Assistant Examiner*—Edny Labbees
(74) *Attorney, Agent, or Firm*—BainwoodHuang

(57) ABSTRACT

A method is performed in an electronic system having (i) hardware configured to perform electronic operations and (ii) an air filter configured to remove contamination from an air stream that cools the hardware. The method, which identifies when to change an air filter, involves obtaining, from a set of particle sensors, a set of sensor signals in response to sensed particles in the air stream. The method further involves generating particle count data and processing the data based on the set of sensor signals, and providing an output signal having one of a first value and a second value based on the particle count data. The output signal indicates that the air filter should be changed when the output signal has the first value. The output signal indicates that the air filter should not be changed when the output signal has the second value.

18 Claims, 5 Drawing Sheets

TECHNIQUES FOR IDENTIFYING WHEN TO CHANGE AN AIR FILTER

BACKGROUND

The typical computer system is susceptible to dust. For example, dust may travel into an area of the computer system containing computer hardware. Such dust may make contact with exposed conductive structures (e.g., dust may gather on adjacent surface traces of a circuit board, on neighboring circuit board pads or device contacts, etc.) and collect moisture causing lowered electrical resistance and perhaps even undesired electrical shorts between the conductive structures. These are known as hygroscopic dust failures. Such a situation may produce disadvantageous results such as corruption of electronic signals, a catastrophic fire, etc.

To prevent dust from entering the hardware areas of computer systems, some manufacturers equip their computer systems with air filters which remove dust from the air entering the systems, e.g., air flows generated by fan assemblies. Once the air filters have collected a certain amount of dust, the air filters no longer reliably allow sufficient air to pass into the computer systems for adequate hardware cooling. To prevent computer systems from overheating, users of the computer systems should change the air filters before the air filters become significantly clogged.

There are a variety of conventional approaches to determining when a user should change an air filter of a computer system. One conventional approach to determining when a user should change an air filter is to use a timer which measures hours of operation. In this approach (hereinafter referred to as the "conventional timer approach"), the user starts a timer (e.g., a background task running on the computer system). After a preset amount of time transpires (e.g., three months), the timer goes off and the computer system displays a notice to the user instructing the user to change the air filter.

In another conventional approach (hereinafter referred to as the "conventional temperature sensing approach"), the computer system includes a temperature sensing circuit which remains silent as long as the temperature within the computer system remains below a preset temperature threshold. When the temperature within the computer system rises above the preset temperature threshold due to clogging of the air filter (i.e., an abnormal temperature rise), the temperature sensing circuit signals the user to change the air filter.

In yet another approach (hereinafter referred to as the "conventional bleed hole approach"), the computer system includes a bleed hole and an anemometer circuit disposed within the bleed hole. When the air filter is clean, the air filter allows sufficient air to pass therethrough, and there is little or no air passing through the bleed hole. Accordingly, the anemometer circuit detects minimal air flow through the bleed hole and remains silent. However, following a period of operation, the capacity of the air filter decreases causing the amount of air passing through the bleed hole to increase. Eventually, the anemometer circuit determines that the air flow through the bleed hole exceeds a preset threshold and signals the user to change the air filter.

SUMMARY

Unfortunately, there are deficiencies to the above-described conventional approaches to determining when a user should change an air filter of a computer system. For example, the above-described conventional timer approach is non-adaptive because it does not take into account differences in the dust level of the surrounding environment. That is, the timer goes off after a fixed period of time elapses regardless of whether the air filter is clean or dirty. As a result, if the computer system operates in a substantially clean environment (e.g., a computer laboratory), the user will change the air filter prematurely. Alternatively, if the computer system operates in a substantially dusty environment (e.g., a post office), the air filter may clog before the timer signals the user to change the air filter thus causing the computer system to overheat and potentially sustain damage due to insufficient air flow.

Additionally, in connection with the above-described conventional temperature sensing approach, the temperature sensing circuit may signal the user to change the air filter even though the air filter is clean. Such a false alarm may occur in response to an increase in temperature which is unrelated to cleanliness of the air filter such as a failing or bad fan, a neighboring device which has overheated due to a damaged or improperly mounted heat sink, etc. Unfortunately, there are many reasons that can contribute to an abnormal temperature rise. Moreover, consistent operation of the temperature sensing circuit is difficult to maintain in certain implementations such as in card cage environments which provide the capability of housing different numbers of circuit boards resulting in different internal air flow patterns and temperature sensing situations.

Furthermore, in connection with the above-described conventional bleed hole approach which utilizes a bleed hole, the computer system may not comply with particular air filtration requirements and standards such as NEBS GR-78-CORE and GR-63-CORE. Also, it may be difficult to define the air flow pattern through the bleed hole for consistent signaling to the user since the amount of air through the bleed hole will vary due to positioning of the bleed hole relative to external structures (e.g., neighboring external obstructions). Additionally, the bleed hole itself may be a source of undesirable dust into the computer system.

In contrast to the above-described conventional approaches to determining when a user should change an air filter of a computer system, an improved technique for identifying when to change the air filter of the electronic system uses particle count information from a set of particle sensors. Monitoring of such particle count information provides a robust and reliable mechanism for determining how much dust has accumulated on the air filter. Moreover, examination of such information alleviates the need to use less-reliable devices such as a timer or a temperature sensor.

In one embodiment, a method is performed in an electronic system having (i) hardware configured to perform electronic operations and (ii) an air filter configured to remove contamination from an air stream that cools the hardware. The method, which identifies when to change an air filter, involves obtaining, from a set of particle sensors, a set of sensor signals in response to sensed particles in the air stream. The method further involves generating particle count data based on the set of sensor signals, and providing an output signal having one of a first value and a second value based on the particle count data. The output signal indicates that the air filter should be changed when the output signal has the first value. The output signal indicates that the air filter should not be changed when the output signal has the second value.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

An improved technique for detecting dust accumulation on an air filter of an electronic system uses particle count information from a set of particle sensors. Examination of such particle count information provides a robust and reliable mechanism for identifying when a user should change the air filter. Moreover, processing of such information alleviates the need to depend on less-accurate devices such as a timer or a temperature sensor.

Figure 1:
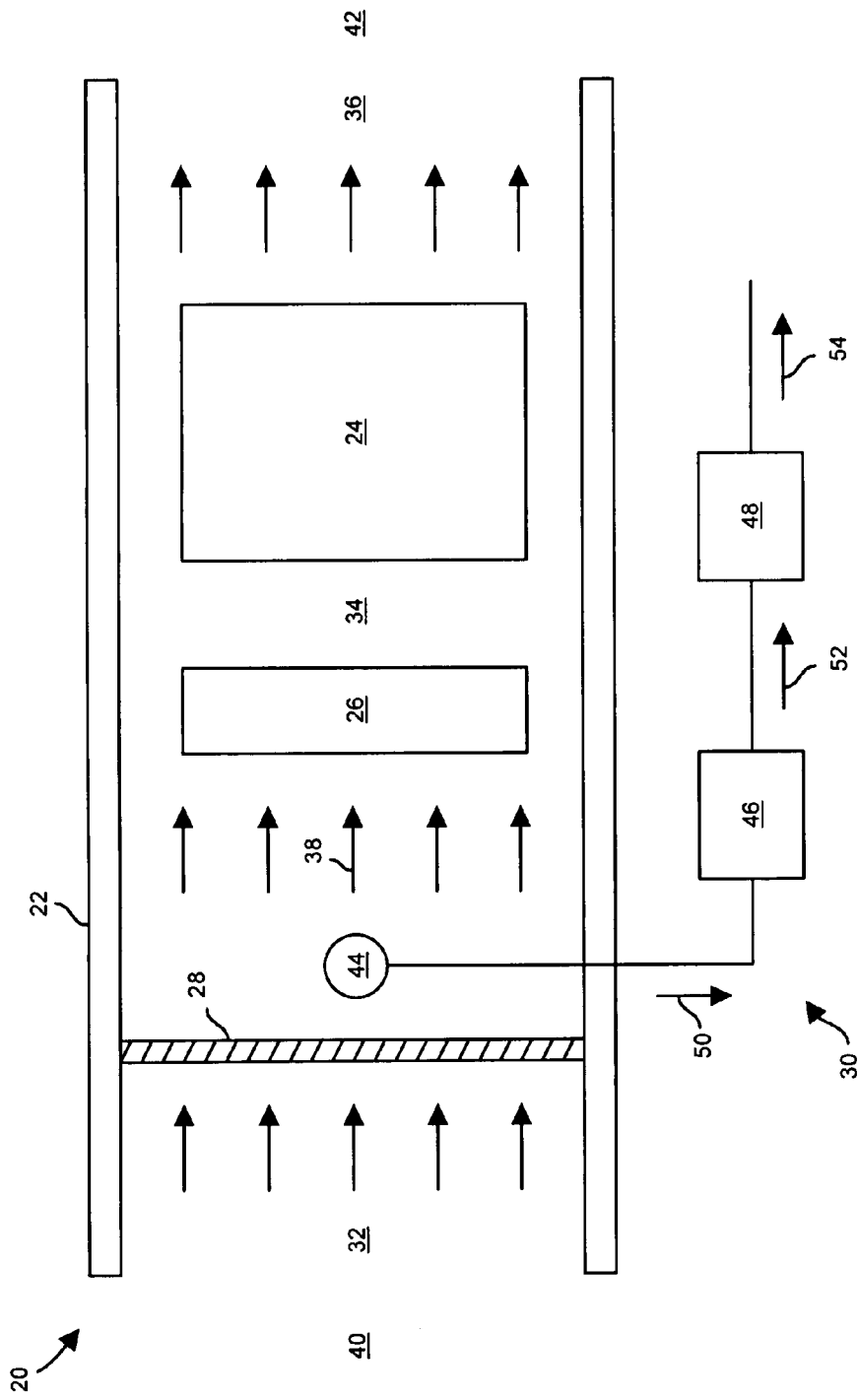
FIG. 1 is a block diagram showing an electronic system having an improved mechanism for detecting dust accumulation.

FIG. 1 shows a general block diagram of an electronic system 20 having an improved mechanism for notifying a user to change an air filter using particle count information from a set of particle sensors. By way of example only, the electronic system 20 is a data communications device (e.g., a router, a switch, a hub, a bridge, a gateway, a firewall, a server, a VoIP device, combinations thereof, etc.) within a computerized network (e.g., a wide area network, a local area network, etc.). While the system 20 is running, circuitry of the electronic system 20 is configured to perform a variety of data communications tasks (e.g., high-speed routing operations, security operations, etc.) within the computerized network.

As shown in FIG. 1, the electronic system 20 includes a housing 22 (shown generally in FIG. 1 as a chassis defining a horizontal pathway), hardware 24, a fan assembly 26, an air filter 28, and an air filter controller 30. The housing 22 defines an inlet portion 32, an enclosed space 34, and an outlet portion 36. The housing 22 mechanically supports the hardware 24, the fan assembly 26, the air filter 28, and at least a portion of the controller 30 (e.g., a set of particle sensors) within the enclosed space 34.

During operation of the electronic system 20, the hardware 24 performs electronic operations (e.g., data communications operations) and the fan assembly 26 concurrently generates an air stream 38 through the enclosed space 34 in order to cool the hardware 24. In particular, the fan assembly 26 draws relatively cool ambient air from an external location 40 adjacent the inlet portion 32 of the housing 22 and moves that air through the air filter 28. The fan assembly 26 further moves that air past the hardware 24, and out to another external location 42 adjacent the exhaust portion 36 of the housing 22. As the air stream 38 passes through the air filter 28, the air filter 28 removes contaminants (i.e., large dust particles and other airborne matter which are prone to clinging to conductive structures). Furthermore, as the air stream 38 passes over the hardware 24, the air stream 38 carries away heat from the hardware 24 thus enabling the hardware 24 to operate within a well-controlled temperature range. Accordingly, the hardware 24 is capable of operating in a substantially-clean, temperature-controlled environment (i) without collecting large dust particles dust and moisture on conductive surfaces, and (ii) and without suffering the associated drawbacks.

The air filter controller 30 is configured to identify when to change the air filter 28 and is configured to operate concurrently with the hardware 24. As shown in FIG. 1, the air filter controller 30 includes a set of particle sensors 44 (shown generally by the reference element 44 in close proximity to the air filter 28 in FIG. 1), processing circuitry 46 and output circuitry 48 which are electrically coupled together in a pipelined manner. In some arrangements, a microprocessor concurrently forms (i) at least part of the hardware 24 configured to perform electronic operations (e.g., network-related tasks), (ii) the processing circuitry 46 configured to generate the particle count data, and (iii) the output circuitry 48 configured to provide the output signal 54.

The set of particle sensors 44 (i.e., one or more particle sensors 44) is disposed adjacent the air filter 28. The set of particle sensors 44 is configured to sense dust particles in the air stream 38 and to provide a set of sensor signals 50 (i.e., one or more sensor signals 50) in response to the sensed dust particles in the air stream 38.

The processing circuitry 46 is configured to generate particle count data 52 based on the set of sensor signals 50, and the output circuitry 48 is configured to provide an output signal 54 having either a first value or a second value based on the particle count data 52. The output signal 54 indicates that a user should change the air filter 28 when the output signal 48 has the first value (e.g., light from a red LED), and that the user should not change the air filter 28 when the output signal 54 has the second value (e.g., light from a green LED). Accordingly, when a user observes that the output signal 54 no longer has the second value, but now has the first value, the user knows that the air filter 28 should be changed.

It should be understood that such notification to the user is accurately based on the operation of the air filter 28 (i.e., particle count information) rather than simply time as in a conventional timer approach, or simply temperature as in a conventional temperature sensing approach. As a result, the determination of whether to change the air filter 28 is well-based on the operation of the air filter 28, and there is little or no risk that the user will change the air filter at the wrong time (e.g., prematurely as in a conventional timer approach) or for the wrong reason (e.g., due to a bad fan as in a conventional heat sensing approach). Moreover, in contrast to a conventional bleed hole approach, the air filter controller 30 of the electronic system 20 is capable of providing such user notification while complying with air filtration requirements and standards such as NEBS GR-78-CORE and GR-63-CORE.

It should be further understood that a variety of configurations are suitable for use by the air filter controller 30. Further details of a first configuration will now be provided with reference to FIG. 2.

Figure 2:
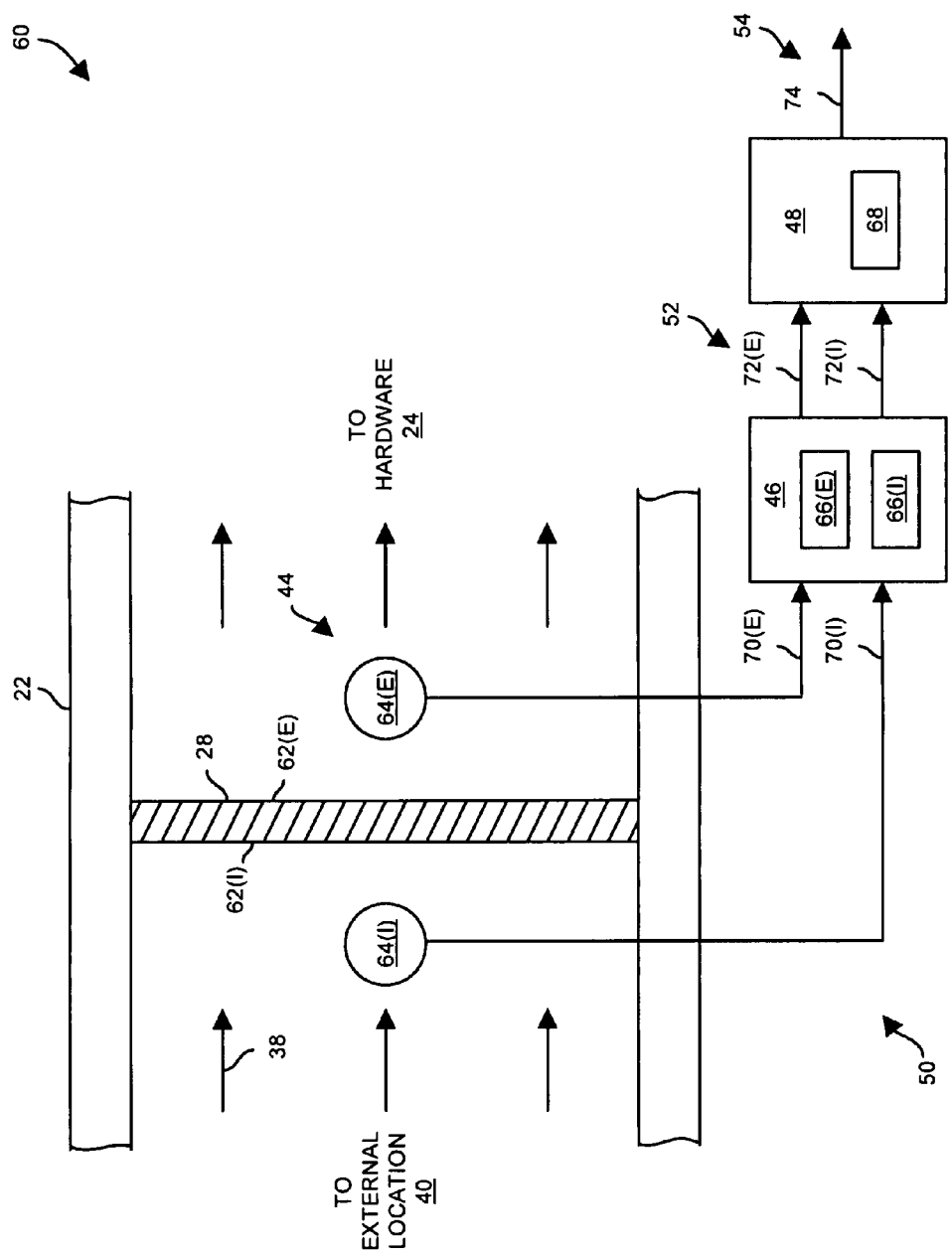
FIG. 2 is a detailed diagram of a portion of the electronic system in accordance with a first configuration.

FIG. 2 shows a portion 60 of the electronic system 20 in accordance with the first configuration. In general, this first configuration considers the air filter 28 to be in acceptable condition when the number of moderately-sized particles (i.e., particles between 3.0 and 5.0 microns in size) flowing toward the air filter 28 is roughly equal to the number of moderately-sized particles flowing from the air filter 28. In this situation, the air filter 28 is initially equipped to capture large-sized particles (i.e., particles larger than 5.0 microns) but porous enough to enable adequate air flow and smaller particles (i.e., particles smaller than 5.0 microns) to pass therethrough for reliable cooling of the hardware 24 (also see FIG. 1).

As shown in FIG. 2, the air filter 28 has an inlet side 62(I) and an exhaust side 62(E). The air stream 38 flows toward the inlet side 62(I) and away from the exhaust side 62(E).

As further shown in FIG. 2, the set of particle sensors 44 includes an inlet-side particle sensor 64(I) and an exhaust-side particle sensor 64(E). The inlet-side particle sensor 64(I) is disposed adjacent the air filter 28 between the external location 40 and the inlet side 62(I) of the air filter 28 (also see FIG. 1), and is configured to sense moderately-sized particles of the air stream 38 flowing from the external location 40 toward the inlet side 62(I) of the air filter 28. Similarly, the exhaust-side particle sensor 64(E) is disposed adjacent the air filter 28 between the exhaust side 62(E) of the air filter 28 and the hardware 24, and is configured to sense moderately-sized particles of the air stream 38 flowing away from the exhaust side 62(E) of the air filter 28 and toward the hardware 24.

As further shown in FIG. 2, the processing circuitry 46 includes, among other things, an inlet counter 66(I) and an exhaust counter 66(E). Additionally, the output circuitry 48 includes, among other things, a memory location 68.

During operation, the inlet-side particle sensor 64(I) provides, as one of the set of sensor signals 50 (also see FIG. 1), an inlet sensor signal 70(I) (e.g., a voltage signal) indicating an amount of sensed moderately-sized particles in the air stream 38 flowing toward the inlet side 62(I) of the air filter 28. In response to the inlet sensor signal 70(I), the inlet counter 66(I) stores an inlet result 72(I) which is a running total of amounts of sensed moderately-sized particles in the air stream 38 flowing toward the inlet side 62(I) of the air filter 28 over a period of time (e.g., one minute).

Similarly, the exhaust-side particle sensor 64(E) provides, as another one of the set of sensor signals 50, an exhaust sensor signal 70(I) indicating an amount of sensed moderately-sized particles in the air stream 38 flowing from the exhaust side 62(E) of the air filter 28. In response to the exhaust sensor signal 70(E), the exhaust counter 66(I) stores an exhaust result 72(E) which is a running total of amounts of sensed moderately-sized particles in the air stream 38 flowing from the exhaust side 62(E) over the period of time.

The output circuitry 48 receives the results 72(I), 72(E) (i.e., reads the contents of the counters 66(I), 66(E)) and produces a difference result which identifies a difference between the inlet result 72(I) and the exhaust result 72(E). The output circuitry 48 stores this difference result as contents in the memory location 68 and further provides, as the output signal 54, a notification signal 74 having (i) a first value when the difference result is above a predetermined threshold and (ii) a second value when the difference result is below the predetermined threshold. Accordingly, when there is not a substantial difference between the amount of moderately-sized particles flowing toward the air filter 28 and flowing from the air filter 28 (i.e., when the difference result is below the predetermined threshold), the air filter 28 is clean and functioning properly. In particular, the air filter 28 is capturing large particles (i.e., particles larger than 5.0 microns), but nevertheless allows sufficient air and smaller particles (i.e., particles smaller than 5.0 microns) to pass therethrough. As a result, the notification signal 74 initially has the second value and the user knows that the air filter 28 does not need replacing.

However, when there is a substantial difference between the amount of the moderately-sized particles flowing toward the air filter 28 and flowing from the air filter 28 (i.e., when the contents of the memory location 68 exceeds the predetermined threshold), the air filter 28 is dirty and requires changing. That is, the air filter 28 is now so clogged that it captures moderately-sized particles and the strength of the air stream 38 is now limited. As a result, the notification signal 74 now has the first value and the user knows that the air filter 28 needs replacing. The output circuitry 48 is capable of holding the notification signal 74 at the first value until the user replaces the air filter 28 (e.g., providing the notification signal 74 to a latching flip-flop which holds the output at the first value until the user resets the flip-flop upon changing the air filter 28, etc.).

In one arrangement, the particle sensors 64(I), 64(E) provide, within the sensor signals 70(I), 70 (E), pulses when moderately-sized particles pass thereby. The counters 66(I), 66(E) increment in response to the pulses within the sensor signals 70(I), 70(E) in order to provide respective running total amounts of particles sensed by the particle sensors 64(I), 64(E). Periodically (e.g., once a minute), the processing circuitry 46 simultaneously resets the counters 66(I), 66(E) so that the contents of the counters 66(I), 66(E) reflect measurements on a per unit of time basis (e.g., moderate-sized particles per minute).

It should be understood that, in some respects, the first configuration is a particle differential scheme involving a comparison of in-flight and out-flight moderate-sized particles. That is, suppose that S1 is the amount of upstream or in-flight particles, and S2 is the amount of downstream or out-flight particles. The performance, F_diff( ), of the air filter 28 is capable of being characterized as follows:

$$F\_diff(t) = fn(S1) - fn(S2)$$

where fn(S1) characterizes sensing of the in-flight particles and fn(S2) characterizes sensing of the out-flight particles. Clearly, fn(S2) becomes weaker (i.e., less moderate-sized particles going through the air filter 28) over time. Such operation results in dust contamination detection on the air filter 28. Further details of a second configuration for the air filter controller 30 (FIG. 1) will now be provided with reference to FIG. 3.

Figure 3:
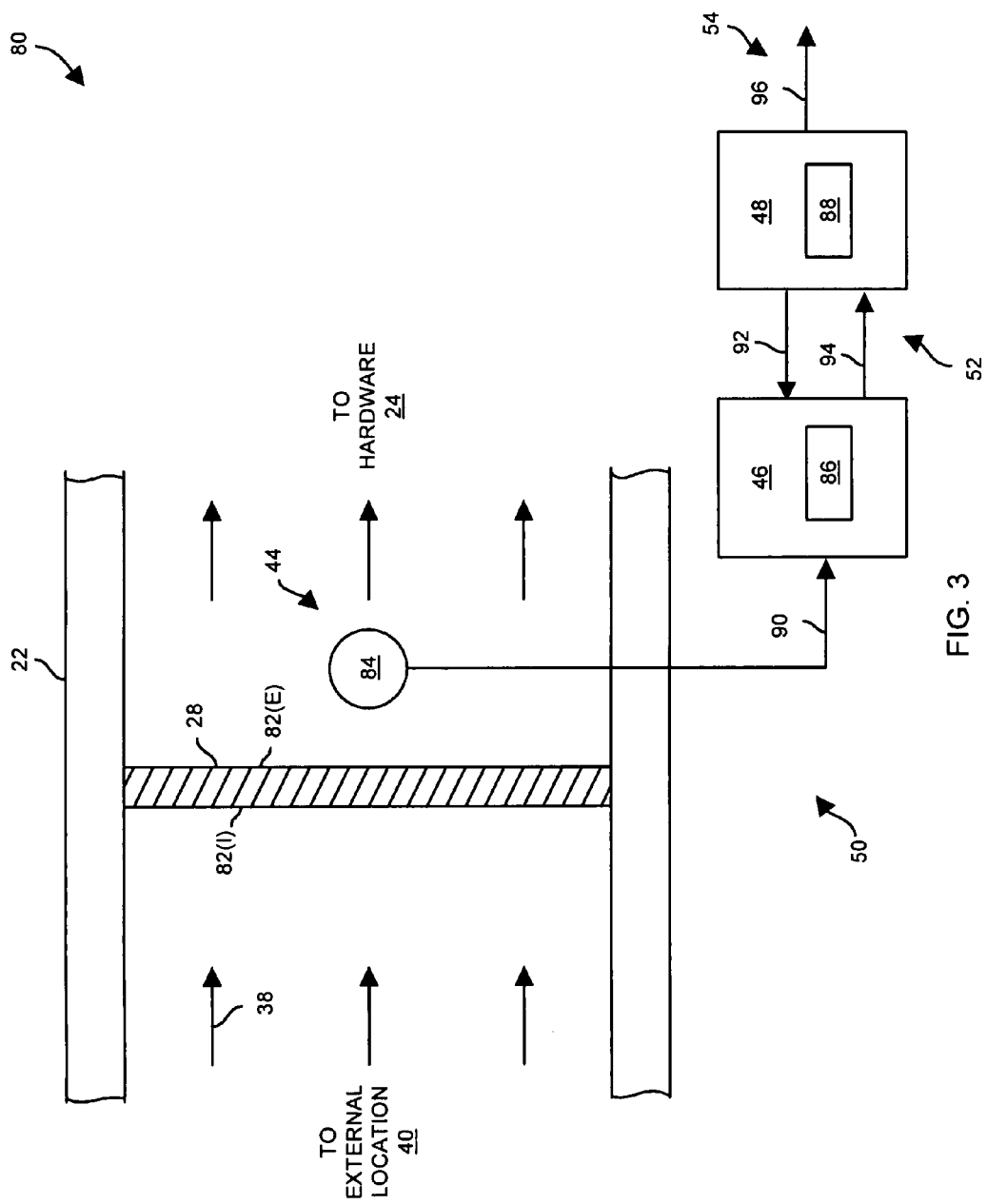
FIG. 3 is a detailed diagram of a portion of the electronic system in accordance with a second configuration.

FIG. 3 shows a portion 80 of the electronic system 20 in accordance with the second configuration. In general, this second configuration considers the air filter 28 to be in acceptable condition when the number of moderately-sized particles (i.e., particles between 3.0 and 5.0 microns in size) flowing from the air filter 28 substantially matches or exceeds a predetermined threshold during a standard amount of time, e.g., the number of moderately-sized particles that would typically pass through a properly functioning air filter or an air filter of acceptable cleanliness in one minute. When the total number of moderately-sized particles flowing from the air filter 28 during this standard unit of time substantially matches or exceeds this predetermined threshold, the air filter 28 is porous enough to enable adequate air flow (as well as moderate-sized and smaller particles) to pass therethrough for reliable cooling of the hardware 24 (also see FIG. 1). However, when the total number of moderately-sized particles flowing from the air filter 28 during this standard unit of time is lower than the predetermined threshold, the air filter 28 capacity has diminished and the air filter 28 is no longer porous enough to enable adequate air flow to pass therethrough (i.e., the air filter 28 is now clogged and captures moderate-sized particles).

As shown in FIG. 3, the air filter 28 has an inlet side 82(I) and an exhaust side 82(E). The air stream 38 flows toward the inlet side 82(I) and away from the exhaust side 82(E).

As further shown in FIG. 3, the set of particle sensors 44 includes an exhaust-side particle sensor 84 which is disposed adjacent the air filter 28 between the exhaust side 82 of the air filter 28 and the hardware 24. The exhaust-side particle sensor 84 is configured to sense moderately-sized particles of the air stream 38 flowing away from the exhaust side 82 of the air filter 28 and toward the hardware 24.

As further shown in FIG. 3, the processing circuitry 46 includes, among other things, an exhaust counter 86. The output circuitry 48 includes, among other things, a memory location 88 which stores the predetermined threshold.

During operation, the exhaust-side particle sensor 84 provides, as one of the set of sensor signals 50, an exhaust sensor signal 90 (e.g., a voltage signal) indicating an amount of sensed moderately-sized particles in the air stream 38 flowing from the exhaust side 82(E) of the air filter 28. The output circuitry 48 provides an initialization signal 92 to the processing circuitry 46 to initialize the exhaust counter 86. In response to the initialization signal 92, the exhaust counter 86 initializes, e.g., sets itself to zero. Next, in response to the exhaust sensor signal 90, the exhaust counter 86 of the processing circuitry 46 updates its contents thus providing a running total of amounts of sensed moderately-sized particles in the air stream 38 flowing from the exhaust side 82(E) over a period of time.

At a set time after the output circuitry 48 provides the initialization signal 92 to initialize the exhaust counter 86, the output circuitry 48 reads the contents of the exhaust counter 86 (i.e., the running total of moderate-sized particles flowing through the air filter 28) and compares the read contents of the exhaust counter 86 to the contents of the memory location 88 (i.e., the predetermined threshold). The transfer of the contents of the exhaust counter 86 is shown as particle count information 94 (i.e., one of the signals 52 in FIG. 1) conveyed from the processing circuitry 46 to the output circuitry 48.

The output circuitry 48 then provides, as the output signal 54, a notification signal 96 having (i) a first value when the running total is below the predetermined threshold and (ii) a second value when the running total is above the predetermined threshold. Accordingly, the user is capable of determining when the air filter 28 is properly functioning and allowing sufficient air flow and moderate-sized particles to flow therethrough in a standard unit of time (i.e., when the notification signal 96 has the second value), and when the air filter 28 is no longer functioning properly and is clogged to the point where sufficient air flow and moderate-sized particles no longer flow therethrough in the standard unit of time (i.e., when the notification signal 96 has the first value).

Following this operation, the output circuitry 48 resends the initialization signal 92 to the processing circuitry 46 to reset the contents of the exhaust counter 86 and waits until the set amount of time (e.g., one minute) to re-examine the exhaust counter 86. This process is repeated in a continuous manner for ongoing user notification. As a result, the output circuitry 48 is capable of continuously monitoring the performance of the air filters 28 as they become clogged and are replaced. A flip-flop is capable of holding the current value of the notification signal 96 until each next comparison.

In one arrangement, the particle sensor 84 provides, within the sensor signal 90, pulses when moderately-sized particles pass thereby. The counter 86 increments in response to the pulses within the sensor signal 90 in order to provide respective running total amounts of particles sensed by the particle sensor 84. At set intervals, the processing circuitry 46 simultaneously resets the exhaust counter 86 so that the contents of the exhaust counter 86 reflects measurements on a per unit of time basis (e.g., out-flowing moderate-sized particles per minute). Further details of a third configuration for the air filter controller 30 (FIG. 1) will now be provided with reference to FIG. 4.

Figure 4:
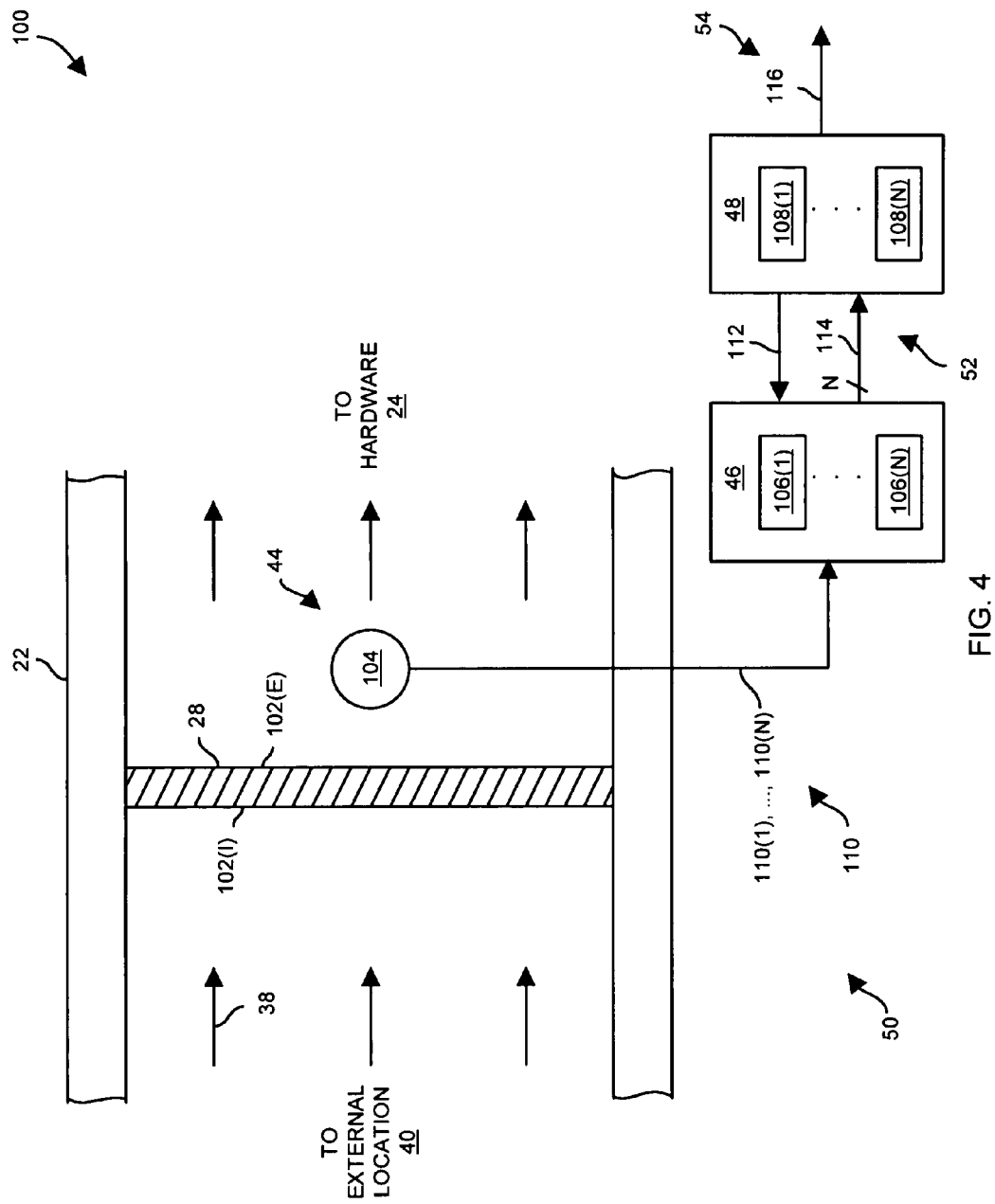
FIG. 4 is a detailed diagram of a portion of the electronic system in accordance with a third configuration.

FIG. 4 shows a portion 100 of the electronic system 20 in accordance with the third configuration. In general, this third configuration compares an operating particle-distribution profile of the air filter 28 to a known particle-distribution profile of a typical air filter (e.g., a particle-distribution profile of a typical acceptable air filter, a particle-distribution profile of a typical clogged air filter, etc.) to determine whether the air filter 28 currently provides adequate air flow or requires changing. Such distribution profiles include particle count information for multiple categories of differently sized particles such as small-sized particles between 0.5 and 3.0 microns in size, and moderate-sized particles which are between 3.0 and 5.0 microns in size. Along these lines, the profile of the air filter 28 in operation initially allows small-sized and moderate-sized particles to pass therethrough while catching large-size particles. However, over time, the air filter 28 collects dust, the capacity of the air filter 28 diminishes and the resulting operating profile of the air filter 28 changes. Eventually, the air filter 28 becomes clogged to the point that it should be replaced in order to guarantee adequate air flow for cooling the hardware 24. At this point, the air filter 28 no longer substantially allows moderate-sized particles to flow through and this condition is easily and accurately identifiable by monitoring the current operating profile of the air filter 28.

As shown in FIG. 4, the air filter 28 has an inlet side 102(I) and an exhaust side 102(E). The air stream 38 flows toward the inlet side 102(I) and away from the exhaust side 102(E).

As further shown in FIG. 4, the set of particle sensors 44 includes an exhaust-side particle sensor 104 which is adjacent the air filter 28 and is disposed between the exhaust side 102(E) of the air filter 28 and the hardware 24. The exhaust-side particle sensor 104 is configured to distinguish between particles of different sizes. In particular, the sensor 104 senses multiple categories of differently-sized particles of the air stream 38 flowing away from the exhaust side 102(E) of the air filter 28 and toward the hardware 24, and provides multiple exhaust sensor signals 110 corresponding to the multiple particle-size categories (e.g., N particle-size categories). In one arrangement, each exhaust sensor signal 110 provides a measurement of particles within a respective particle size range flowing from the exhaust side 102(E) of the air filter 28 toward the hardware 24 (e.g., one or more microprocessors for performing data communications operations within the computerized network).

As further shown in FIG. 4, the processing circuitry 46 includes, among other things, a set of exhaust counters 106(1), . . . , 106(N) (collectively, exhaust counters 106) which is configured to store a current (or real-time) particle-distribution profile of the air filter 28. The output circuitry 48 includes, among other things, a set of memory locations 108(1), . . . , 108(N) (collectively, memory locations 108) which stores a predetermined particle-distribution profile of an acceptable air filter.

During operation, the exhaust-side particle sensor 104 provides a set of exhaust sensor signals 110(1), . . . , 110(N)

(collectively, sensor signals 110) indicating an amount of sensed moderately-sized particles in the air stream 38 flowing from the exhaust side 102(E) of the air filter 28. The output circuitry 48 provides an initialization signal 112 to the processing circuitry 46 to initialize the exhaust counters 106. In response to the initialization signal 112, the exhaust counters 106 initialize, e.g., the exhaust counter 106 set themselves to zero. Next, in response to the exhaust sensor signals 110, the exhaust counters 106 of the processing circuitry 46 update their respective contents thus providing running totals of amounts of sensed differently-sized particles in the air stream 38 flowing from the exhaust side 102(E) over the period of time. For example, the counter 106(1) provides a running total of amounts of small-sized particles, the counter 106(2) provides a running total of amounts of moderate-sized particles, and so on.

At a set time after the output circuitry 48 provides the initialization signal 112 to initialize the exhaust counters 106, the output circuitry 48 reads the contents of the exhaust counters 106 and compares the read contents to the acceptable-predetermined air filter profile stored in the memory locations 108 (e.g., by performing a count-by-count comparison, by performing statistical analysis, etc.). The transfer of the contents of the exhaust counters 106 is shown as particle count information 114 (i.e., N signals 52, also see FIG. 1) conveyed from the processing circuitry 46 to the output circuitry 48.

The output circuitry 48 then provides, as the output signal 54, a notification signal 116 having (i) a first value when the current/operating particle-distribution profile has deviated from the acceptable particle-distribution profile by a preset amount and (ii) a second value when the current/operating profile has not deviated from the acceptable profile by a preset amount. Accordingly, the user is capable of determining when the air filter 28 operates to perform in a manner similar to an acceptable profile (i.e., when the notification signal 116 has the second value), and when the air filter 28 is no longer performs in a manner similar to the acceptable profile (i.e., when the notification signal 116 has the first value).

Following this operation, the output circuitry 48 resends the initialization signal 112 to the processing circuitry 46 to reset the contents of the exhaust counter 106 and waits until the set amount of time (e.g., one minute) to re-examine the exhaust counter 106. This process is repeated in a continuous manner for ongoing user notification. As a result, the output circuitry 48 is capable of continuously monitoring the current performance of the air filters 28 in an ongoing manner to ensure reliable detection of when the air filter 28 becomes clogged and requires replacing.

In one arrangement, the particle sensor 104 provides, within the sensor signals 110, pulses when moderately-sized particles pass thereby. The counters 106 increment in response to the pulses within the respective sensor signals 110 in order to provide respective running total amounts of particles sensed by the particle sensor 104. At set intervals, the processing circuitry 46 simultaneously resets the exhaust counter 106 so that the contents of the exhaust counter 106 reflects measurements on a per unit of time basis (e.g., particular-sized particles per minute).

It should be understood the above-described operation of the third configuration involved a comparison between a current particle-distribution profile of the air filter 28 and a preset particle-distribution profile which is acceptable (e.g., a known profile for a clean air filter). When the current profile substantially deviates from the preset profile, the output circuitry 48 signals the user to change the air filter 28.

Alternatively, the third configuration is capable of comparing the current particle-distribution profile of the air filter 28 to a preset particle-distribution profile which is unacceptable (e.g., a known profile of a clogged air filter). In this situation, when the current profile substantially matches the preset profile, the output circuitry 48 signals the user to change the air filter 28. In either situation, such comparisons are capable of involving a series of microprocessor operations (e.g., simple count comparisons, more-complex probability and statistics analysis, etc.).

It should be understood that, in some arrangements, the operations of the processing circuitry 46 and the output circuitry 48 are performed by a microprocessor which also forms a portion of the hardware 24.

It should be further understood that, in some respects, the third configuration is a pulse-occupancy-time involving a statistical approach to determining when the air filter is contaminated. That is, suppose that profiles P1 and P2 are pulse occupancy time per unit time (%) each of which includes data regarding the presence of two distinctive particle sizes and counts. In particular, suppose that the profile P1 represents the dust probability distribution of a fresh and clean air filter, and that the profile P2 represents the dust probability of a contaminated air filter. During operation of the electronic system 20, the profile of the air filter 28 will diverge from the profile P1 and will converge towards the profile P2. In some arrangements, the air filter controller 30 is configured to monitor divergence of the current profile of the air filter 28 from the clean profile P1 (e.g., by applying statistical algorithms to particle count data). In other arrangements, the air filter controller 30 is configured to monitor convergence of the current profile of the air filter 28 to the contaminated profile P2). In yet other arrangements, the air filter controller 28 is configured to monitor both divergence from the clean profile P1 and convergence to the contaminated profile P2. In any of the arrangements, the sensitivity of each particle sensor 44 is preferably capable of being finely tuned for precise profile generation. Further details of the operation of the electronic system 20 will now be provided with reference to FIG. 5.

Figure 5:
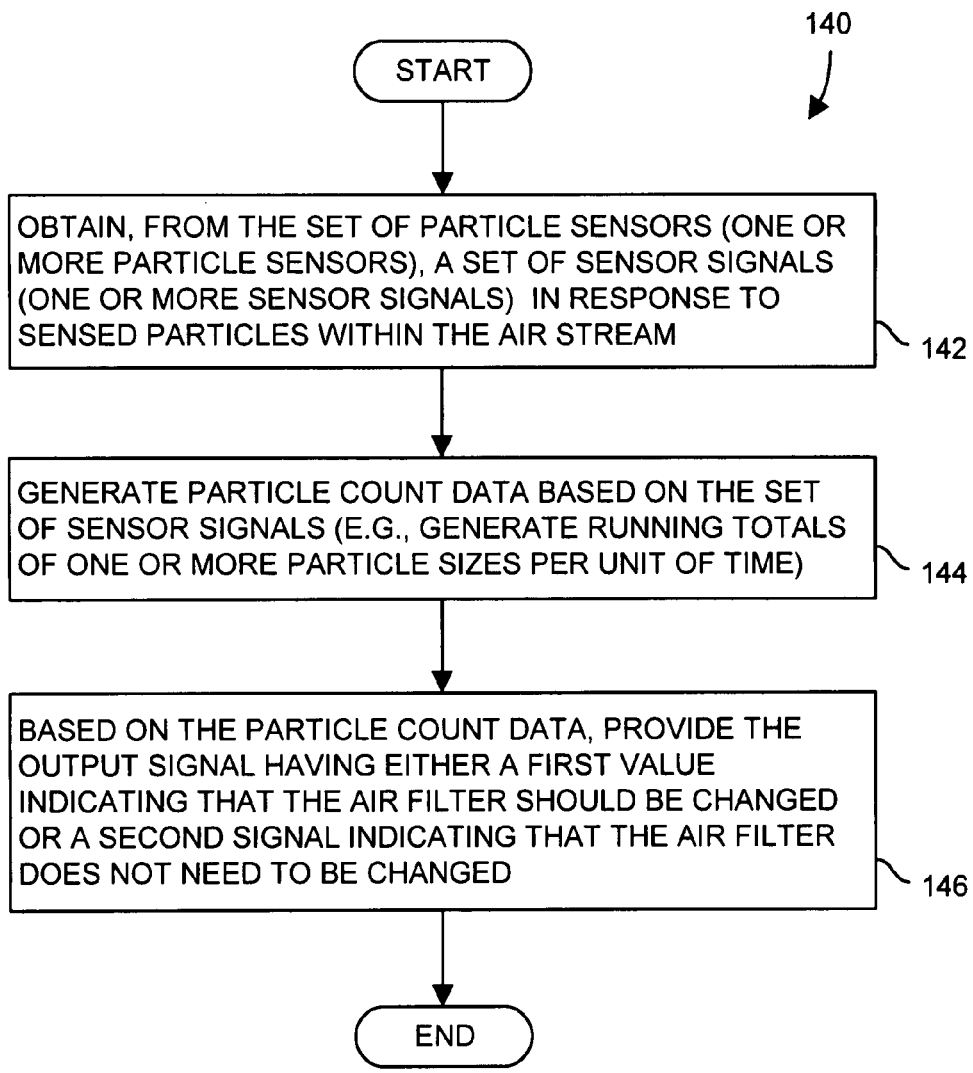
FIG. 5 is a flowchart of a procedure for detecting dust accumulation which is performed by a portion of the electronic system of FIG. 1.

FIG. 5 is a flowchart of a procedure 140 for detecting dust accumulation which is performed by the processing and output circuitry 46, 48 of the air filter controller 50 (also see FIG. 1). In step 142, the processing circuitry 46 obtains, from the set of particle sensors 44, the set of sensor signals 50 in response to sensed particles in the air stream 38.

In step 144, the processing circuitry 46 generates particle count data (i.e., signals 52) based on the set of sensor signals 50. For instance, the processing circuitry 46 tabulates running totals of one or more particle sizes on a per unit of time basis (e.g., per minute, per 10 minutes, per hour, etc.).

In step 146, the output circuitry 48 provides the output signal 54 having one of a first value and a second value based on the particle count data 52. The output signal 52 indicates that the air filter 28 should be changed when the output signal 54 has the first value, and that the air filter 28 should not be changed when the output signal has the second value.

As mentioned above, an improved technique for identifying when to change an air filter 28 of an electronic system 30 (e.g., a data communications device) uses particle count information from a set of particle sensors 44. Monitoring of such particle count information provides a robust and reliable mechanism for determining how much dust has accumulated on the air filter 28, and thus whether the air filter 28 requires changing. Moreover, such determination is more accurate due to actual assessment of air filter operation and, thus, alleviates the need to use less-reliable devices such as a timer or a temperature sensor.

While this invention has been particularly shown and described with references to preferred embodiments thereof, it will be understood by those skilled in the art that various changes in form and details may be made therein without departing from the spirit and scope of the invention as defined by the appended claims.

For example, the output signal 54 was described above as providing different LED colors to signal the user by way of example only. Other signaling mechanisms for notifying the user to change the air filter 28 are suitable for use as well such as such as a noise emitting device, a window on a computer display, and so on.

Additionally, the electronic system 20 was described above as being a data communications device for illustration purposes. Other types of systems are suitable for use as well such as general purpose computers, fiber optic communications systems, wireless communications systems, automotive systems, custom real-time systems, etc.

Moreover, different particle sensors are suitable for use for the set of particle sensors 44. In particular, the attention to particles within the range of 3.0 microns to 5.0 microns are interesting in the context of a computerized system. However, in an automotive environment, detection of different size particles (e.g., larger particles) may provide improved results.

Furthermore, it should be understood that the placement of the air filter 28, the fan assembly 26 and the hardware 24 were shown in the order of FIG. 1 by way of example only. Other orders are suitable for use as well such as where the fan assembly 26 is before the air filter, and forces air through the air filter 28 toward the hardware 24. As another example, the fan assembly 26 is capable of being last in line to draw air through the air filter 24 and past the hardware 24. Other orders are suitable for use as well.

Additionally, it should be understood that the pathway for the air stream 38 was shown in a simplified manner flowing from left to right in FIG. 1. Other arrangements are suitable for use as well such as vertical orientations, non-straight orientations, etc. For example, all of the earlier-described configurations are suitable for card cage environments regardless of the number of circuit boards (i.e., hardware 24) residing within the card cages, regardless of the orientations of the circuit boards, and regardless of the directions of the air streams 38 through the card cages.

Furthermore, it should be understood that the set of signals 50 from the set of particle sensors 44 was described above as being pulses by way of example only. Other signaling formats are suitable for use as well such as analog or digital voltage signals (i.e., different voltages representing different particle sizes), current signals, fiber optic signals, wireless signals, etc.

Additionally, it should be understood that the above-described improved techniques are not necessarily limited to electronics or a computer system. Rather, such techniques are capable of being implemented on any system involving the use of filters (e.g. house-hold furnaces, automotive power trains, or bio-medical industry, etc.).

What is claimed is:

1. In an electronic system having (i) hardware configured to perform electronic operations and (ii) an air filter configured to remove contamination from an air stream that cools the hardware, a method for identifying when to change the air filter, the method comprising:
   obtaining, from a set of particle sensors, a set of sensor signals in response to sensed particles in the air stream;
   generating particle count data based on the set of sensor signals; and
   providing an output signal having one of a first value and a second value based on the particle count data, the output signal indicating that the air filter should be changed when the output signal has the first value, and the output signal indicating that the air filter should not be changed when the output signal has the second value;
   wherein the air filter has an inlet side and an exhaust side, the air stream flowing toward the inlet side and from the exhaust side; wherein the set of sensor signals includes an inlet sensor signal and an exhaust sensor signal; wherein the set of particle sensors includes (i) an inlet-side particle sensor disposed between an external air source and the inlet side of the air filter, the inlet-side particle sensor being configured to provide the inlet sensor signal, and (ii) an exhaust-side particle sensor disposed between the hardware and the exhaust side of the air filter, the exhaust-side particle sensor being configured to provide the exhaust sensor signal; and wherein generating the particle count data includes:
      generating an inlet result based on the inlet sensor signal, the inlet result representing a quantity of particles flowing toward the air filter in a particular unit of time, and
      generating an exhaust result based on the exhaust sensor signal, the exhaust result representing a quantity of particles flowing from the air filter in the particular unit of time;
   wherein providing the output signal includes:
      producing a difference result which identifies a difference between the inlet result and the exhaust result,
      initially providing the second value in the output signal when the difference result is below a predetermined threshold, and
      providing the first value in the output signal once the difference result exceeds the predetermined threshold.

2. The method of claim 1 wherein generating the particle count data includes:
   initializing contents of a counter and updating the contents of the counter based on the exhaust sensor signal, the contents of the counter representing a quantity of particles within a particular particle size range flowing from the air filter in a particular unit of time.

3. The method of claim 2 wherein providing the output signal includes:
   comparing the contents of the counter to a predetermined threshold;
   initially providing the second value in the output signal when the contents of the counter do not exceed the predetermined threshold; and
   providing the first value in the output signal once the contents of the counter exceed the predetermined threshold.

4. The method of claim 1 wherein the set of sensor signals includes multiple exhaust sensor signals; the exhaust-side particle sensor being configured to provide the multiple exhaust sensor signals; and wherein generating the particle count data includes:
   initializing contents of counters and updating the contents of the counters based on the multiple exhaust sensor signals, the contents of the counters representing respective quantities of particles within respective particle size ranges flowing from the air filter in a particular unit of time.

5. The method of claim 4 wherein providing the output signal includes:
   forming a particle size distribution profile from the contents of the counters;
   comparing the formed particle size distribution profile to a predetermined particle size distribution profile, the predetermined particle size distribution profile corresponding to unacceptable filter performance;
   initially providing the second value in the output signal when the formed particle size distribution profile and the predetermined particle size distribution profile do not significantly match; and
   providing the first value in the output signal once the formed particle size distribution profile and the predetermined particle size distribution profile significantly match.

6. The method of claim 4 wherein providing the output signal includes:
   forming a particle size distribution profile from the contents of the counters;
   comparing the formed particle size distribution profile to a predetermined particle size distribution profile, the predetermined particle size distribution profile corresponding to acceptable filter performance;
   initially providing the second value in the output signal when the formed particle size distribution profile and the predetermined particle size distribution profile significantly match; and
   providing the first value in the output signal once the formed particle size distribution profile and the predetermined particle size distribution profile do not significantly match.

7. The method of claim 1 wherein the hardware is configured to perform data communications operations within a computerized network, and wherein the method further comprises:
   running the hardware to perform the data communications operations within the computerized network while concurrently providing the output signal to indicate whether the air filter, which is configured to remove contamination from the air stream that cools the hardware, should be changed.

8. The method of claim 7 wherein the wherein the air filter has an inlet side and an exhaust side, the air stream flowing toward the inlet side and from the exhaust side; wherein the set of particle sensors includes an exhaust-side particle sensor disposed between the hardware and the exhaust side of the air filter; and wherein obtaining the set of sensor signals includes:
   acquiring multiple exhaust sensor signals from the exhaust particle sensor, each exhaust sensor signal providing a measurement of particles within a respective particle size range flowing from the exhaust side of the air filter toward the hardware configured to perform the data communications operations within the computerized network.

9. The method of claim 1 wherein the hardware includes data communications circuitry configured to transfer point-to-point communications between two other devices within a computerized network; and wherein the method further comprises:
   selectively enabling and disabling operation of the data communications circuitry based on the output signal.

10. An electronic system, comprising:
   hardware configured to perform electronic operations;
   an air filter configured to remove contamination from an air stream that cools the hardware; and
   a controller configured to identify when to change the air filter, the controller including:
     a set of particle sensors configured to sense particles in the air stream and provide a set of sensor signals in response to sensed particles in the air stream;
     processing circuitry coupled to the set of particle sensors, the processing circuitry being configured to generate particle count data based on the set of sensor signals, and
     output circuitry coupled to the processing circuitry, the output circuitry being configured to provide an output signal having one of a first value and a second value based on the particle count data, the output signal indicating that the air filter should be changed when the output signal has the first value, and the output signal indicating that the air filter should not be changed when the output signal has the second value
   wherein the hardware is configured to perform data communications operations within a computerized network while the controller concurrently provides the output signal to indicate whether the air filter, which is configured to remove contamination from the air stream that cools the hardware, should be changed;
   wherein the air filter has an inlet side and an exhaust side, the air stream flowing toward the inlet side and from the exhaust side; wherein the set of sensor signals includes an inlet sensor signal and an exhaust sensor signal; wherein the set of particle sensors includes (i) an inlet-side particle sensor disposed between an external air source and the inlet side of the air filter, the inlet-side particle sensor being configured to provide the inlet sensor signal, and (ii) an exhaust-side particle sensor disposed between the hardware and the exhaust side of the air filter, the exhaust-side particle sensor being configured to provide the exhaust sensor signal;
   wherein the processing circuitry, when generating the particle count data, is configured to:
     generate an inlet result based on the inlet sensor signal, the inlet result representing a quantity of particles flowing toward the air filter in a particular unit of time, and
     generate an exhaust result based on the exhaust sensor signal, the exhaust result representing a quantity of particles flowing from the air filter in the particular unit of time; and
   wherein the output circuitry, when providing the output signal, is configured to:
     produce a difference result which identifies a difference between the inlet result and the exhaust result,
     initially provide the second value in the output signal when the difference result is below a predetermined threshold, and
     provide the first value in the output signal once the difference result exceeds the predetermined threshold.

11. The electronic system of claim 10 wherein the processing circuitry, when generating the particle count data, is configured to:
   initialize contents of a counter and update the contents of the counter based on the exhaust sensor signal, the contents of the counter representing a quantity of particles within a particular particle size range flowing from the air filter in a particular unit of time.

12. The electronic system of claim 10 wherein the set of sensor signals includes multiple exhaust sensor signals, the exhaust-side particle sensor being configured to provide the multiple exhaust sensor signals; wherein the processing circuitry, when generating the particle count data, is configured to:

initialize contents of counters and update the contents of the counters based on the multiple exhaust sensor signals, the contents of the counters representing respective quantities of particles within respective particle size ranges flowing from the air filter in a particular unit of time; and wherein the output circuitry is further configured to:

form a particle size distribution profile from the contents of the counters, compare the formed particle size distribution profile to a predetermined particle size distribution profile, the predetermined particle size distribution profile corresponding to unacceptable filter performance, initially provide the second value in the output signal when the formed particle size distribution profile and the predetermined particle size distribution profile do not significantly match; and provide the first value in the output signal once the formed particle size distribution profile and the predetermined particle size distribution profile significantly match.

13. The electronic system of claim 10 wherein the set of sensor signals includes multiple exhaust sensor signals; the exhaust-side particle sensor being configured to provide the multiple exhaust sensor signals; wherein the processing circuitry, when generating the particle count data, is configured to:

initialize contents of counters and update the contents of the counters based on the multiple exhaust sensor signals, the contents of the counters representing respective quantities of particles within respective particle size ranges flowing from the air filter in a particular unit of time; and wherein the output circuitry is further configured to:

form a particle size distribution profile from the contents of the counters, compare the formed particle size distribution profile to a predetermined particle size distribution profile, the predetermined particle size distribution profile corresponding to acceptable filter performance, initially provide the second value in the output signal when the formed particle size distribution profile and the predetermined particle size distribution profile significantly match, and provide the first value in the output signal once the formed particle size distribution profile and the predetermined particle size distribution profile do not significantly match.

14. The electronic system of claim 10 wherein the set of particle sensors, when providing the set of sensor signals, is configured to:

output multiple exhaust sensor signals, each exhaust sensor signal providing a measurement of particles within a respective particle size range flowing from the exhaust side of the air filter toward the hardware which is configured to perform the data communications operations within the computerized network.

15. The electronic system of claim 10 wherein a microprocessor concurrently forms (i) at least part of the hardware configured to perform electronic operations, (ii) the processing circuitry configured to generate the particle count data, and (iii) the output circuitry configured to provide the output signal.

16. The electronic system of claim 10 wherein the hardware includes data communications circuitry configured to transfer point-to-point communications between two other devices within a computerized network; and wherein the controller further comprises:

switching circuitry coupled to the output circuitry, the switching circuitry being configured to selectively enable and disable operation of the data communications circuitry based on the output signal.

17. An electronic system, comprising:

hardware configured to perform electronic operations;

an air filter configured to remove contamination from an air stream that cools the hardware; and a controller configured to identify when to change the air filter, the controller including:

means for sensing particles in the air stream and providing a set of sensor signals in response to sensed particles in the air stream, processing circuitry coupled to the means for sensing and providing, the processing circuitry being configured to generate particle count data based on the set of sensor signals, and output circuitry coupled to the processing circuitry, the output circuitry being configured to provide an output signal having one of a first value and a second value based on the particle count data, the output signal indicating that the air filter should be changed when the output signal has the first value, and the output signal indicating that the air filter should not be changed when the output signal has the second value wherein the air filter has an inlet side and an exhaust side, the air stream flowing toward the inlet side and from the exhaust side: wherein the set of sensor signals includes an inlet sensor signal and an exhaust sensor signal: wherein the means for sensing and providing includes (i) an inlet-side particle sensor disposed between an external air source and the inlet side of the air filter, the inlet-side particle sensor being configured to provide the inlet sensor signal, and (ii) an exhaust-side particle sensor disposed between the hardware and the exhaust side of the air filter, the exhaust-side particle sensor being configured to provide the exhaust sensor signal: wherein the processing circuitry, when generating the particle count data, is configured to:

generate an inlet result based on the inlet sensor signal, the inlet result representing a quantity of particles flowing toward the air filter in a particular unit of time, and generate an exhaust result based on the exhaust sensor signal, the exhaust result representing a quantity of particles flowing from the air filter in the particular unit of time; and wherein the output circuitry, when providing the output signal, is configured to:

produce a difference result which identifies a difference between the inlet result and the exhaust result, initially provide the second value in the output signal when the difference result is below a predetermined threshold, and provide the first value in the output signal once the difference result exceeds the predetermined threshold.

18. The electronic system of claim 17 wherein the hardware is configured to perform data communications operations within a computerized network while the controller concurrently provides the output signal to indicate whether the air filter, which is configured to remove contamination from the air stream that cools the hardware, should be changed.

* * * * *